United States Patent [19]

Cottman

[11] Patent Number: 5,068,439

[45] Date of Patent: Nov. 26, 1991

[54] N-SUBSTITUTED PHENYLENEDIAMINE COMPOUNDS

[75] Inventor: Kirkwood S. Cottman, Akron, Ohio

[73] Assignee: The Goodyear Tire & Rubber Company, Akron, Ohio

[21] Appl. No.: 596,455

[22] Filed: Oct. 12, 1990

Related U.S. Application Data

[62] Division of Ser. No. 490,211, Mar. 8, 1990, Pat. No. 4,968,843.

[51] Int. Cl.$^5$ ............................................. C07C 211/27
[52] U.S. Cl. ..................................... 564/434; 564/346
[58] Field of Search ................................. 564/346, 434

[56] References Cited

U.S. PATENT DOCUMENTS

| | | | |
|---|---|---|---|
| 1,867,105 | 7/1932 | Schirmacher et al. | 552/301 |
| 3,873,459 | 3/1975 | Pawlak et al. | 252/51.5 A |
| 3,875,227 | 4/1975 | Kroll et al. | 564/99 |
| 3,882,186 | 5/1975 | Cain et al. | 260/780 |
| 4,017,544 | 4/1977 | Mullins | 564/434 |
| 4,045,170 | 8/1977 | Kalopississ et al. | 552/302 |
| 4,355,180 | 10/1982 | Goetz et al. | 564/396 |
| 4,429,157 | 1/1984 | Disteldorf et al. | 564/396 |

FOREIGN PATENT DOCUMENTS

| | | | |
|---|---|---|---|
| 0453546 | 12/1948 | Canada | 564/397 |
| 0072575 | 8/1982 | European Pat. Off. | |
| 125343 | 3/1980 | Japan | |
| 0774794 | 5/1957 | United Kingdom | 552/301 |
| 835669 | 8/1958 | United Kingdom | |
| 900617 | 4/1959 | United Kingdom | |
| 2025958 | 1/1980 | United Kingdom | |

OTHER PUBLICATIONS

Journal of Organic Chemistry, vol. 36, No. 23, 1971, pp. 3497-3501; J. Figueras et al., "The Synthesis and Spectral Properties of Some N-Substituted Derivatives of Phenol Blue".
Chem. Abs. 31632g, "Meta-Phenylenediamines . . . ", Bugaut, Andree.
Gelling, I. R. et al., "Plastics and Rubber Processing", Sep., pp. 83-86 (1977).
Radel, R. J. et al., Ind. Eng. Chem. Prod. Res. Dev., 21, 566-570 (1982).

Primary Examiner—Robert W. Ramsuer
Assistant Examiner—Jessica Nguyen
Attorney, Agent, or Firm—Bruce J. Hendricks

[57] ABSTRACT

The present invention relates to a process for the preparation of a N-substituted phenylenediamine of the formula:

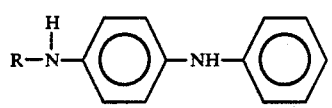

(I)

comprising reacting N-phenylquinoneimine of the formula:

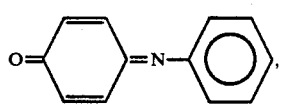

(II)

with a primary amine of the formula:

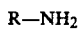

R—NH$_2$ (III), wherein the molar ratio of II to III in the reaction mixture ranges from about 1:1 to 1:10; and wherein R is selected from the group of radicals consisting of alkyls having 1 to 20 carbon atoms, cycloalkyls having 6 to 8 carbon atoms and radicals of the structural formula:

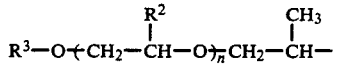

wherein R$^2$ may be the same or different and is independently selected from the group of radicals consisting of hydrogen and an alkyl having 1 carbon atom, R$^3$ is selected from the group of radicals consisting of an alkyl having 1 to 12 carbon atoms and n is an integer of from 0 to 6. The present process is characterized by its excellent yields of high purity N-substituted phenylenediamines.

2 Claims, No Drawings

N-SUBSTITUTED PHENYLENEDIAMINE COMPOUNDS

This is a division of application Ser. No. 07/490,211, filed on Mar. 8, 1990, which is now U.S. Pat. No. 4,968,843 issued Nov. 16, 1990.

BACKGROUND OF THE INVENTION

The present invention relates to a unique method for preparing N-substituted phenylenediamines from N-phenylquinoneimine. N-substituted phenylenediamines are useful as in the production of drugs, agricultural products, and useful as dyes, antioxidants, antiozonants, gel inhibitors and polymerization inhibitors for rubber.

N-substituted phenylenediamines have been made by a variety of methods known to those skilled in the art. For example, Japanese Application 125343-1981 discloses a process for the preparation of phenylenediamines or its N-substitution product by reacting aminophenol or its N-substitution product with (a) ammonia, primary amine or secondary amine in the presence of an acidic catalyst and polycyclic aromatic compound. The process disclosed in Japanese Application No. 125343-1981 is characterized by a one step, one pot procedure and suggests via gas chromatography that yields are upwards to 50 percent. However, preparation of the products by this procedure would necessitate the use of elaborate distillation equipment to remove the polycyclic aromatic compounds that are employed. The removal of the polycyclic aromatic compounds further contributes to the expense of manufacturing the N-substituted phenylenediamine. Since demand for N-substituted phenyenediamines is on the increase with their wide-spread applications, there is a need for a new and more efficient process for their production.

SUMMARY OF THE INVENTION

The present invention relates to a process for the preparation of N-substituted phenylenediamines by reacting a reaction mixture of a N-phenylquinoneimine, and a primary amine.

DETAILED DESCRIPTION OF THE PREFERRED EMBODIMENTS

There is disclosed a process for the preparation of a N-substituted phenylenediamine of the formula:

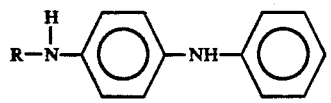
(I)

comprising reacting N-phenylquinoneimine of the formula:

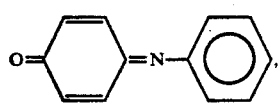
(II)

with a primary amine of the formula:

    (III)

wherein the molar ratio of II to III in the reaction mixture ranges from about 1:1 to 1:10: and wherein R is selected from the group of radicals consisting of alkyls having 1 to 20 carbon atoms, cycloalkyls having 6 to 8 carbon atoms and radicals of the structural formula:

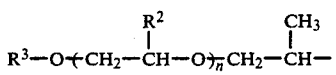

wherein $R^2$ may be the same or different and is independently selected from the group of radicals consisting of hydrogen and an alkyl having 1 carbon atom, $R^3$ is selected from the group of radicals consisting of an alkyl having 1 to 12 carbon atoms and n is an integer of from 0 to 6.

There also is disclosed a process for the preparation of a N-substituted phenylenediamine of the formula:

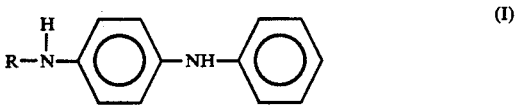
(I)

comprising (a) oxidizing hydroxydiphenylamine to form a N-phenylquinoneimine of the formula:

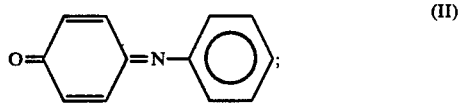
(II)

(b) isolating said N-phenylquinoneimine; and (c) reacting said N-phenylquinoneimine in a reaction mixture containing a primary amine of the formula:

R—NH$_2$    (III).

and the molar ratio of II to III in the reaction mixture ranges from about 1:1 to 1:10; and wherein R is selected from the group of radicals consisting of alkyls having 1 to 20 carbon atoms, cycloalkyls having 6 to 8 carbon atoms and radicals of the structural formula:

wherein $R^2$ may be the same or different and is independently selected from the group of radicals consisting of hydrogen and an alkyl having 1 carbon atom, $R^3$ is selected from the group of radicals consisting of an alkyl having 1 to 12 carbon atoms and n is an integer of from 0 to 6. Preferably $R^3$ is selected from the group of alkyl having 1 or 2 carbon atoms and n is preferably 0 or 1.

In addition, there is disclosed a N-substituted phenylenediamine of the formula:

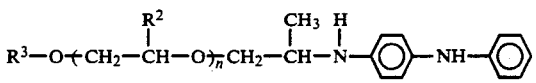

wherein $R^2$ may be the same or different and is independently selected from the group of radicals consisting of hydrogen and an alkyl having 1 carbon atom, $R^3$ is selected from the group of radicals consisting of an alkyl having 1 to 12 carbon atoms and n is an integer of from 0 to 6. These N-substituted phenylenediamines have utility as antidegradants in rubber.

With respect to the above formulae, preferably R is selected from the group of radicals consisting of alkyls having 3 to 8 carbon atoms and cycloalkyls having 6 carbon atoms.

The starting materials for the reaction are N-phenylquinoneimine and the primary amine. In a preferred embodiment, the N-phenylquinoneimine reactant does not contain more than 5 weight percent hydroxydiphenylamine. In the most preferred embodiment, no or only trace amounts will be present. With an increasing amount of hydroxydiphenylamine, there is an increasing hindrance of completion of the reaction to yield the desired product.

The N-phenylquinoneimine may be prepared by the simple oxidation of hydroxydiphenylamine. For example, the hydroxydiphenylamine may be dissolved in a suitable solvent and oxidized. Examples of solvents which may be used include acetone, methylisobutylketone, methylenechloride, tetrahydrofuran and toluene. Preferably a water soluble solvent is used such as the acetone. The hydroxyphenylamine is oxidized with an oxidizing agent. Representative oxidizing agents include sodium dichromate or potassium dichromate in conjunction with an acid, such as acetic acid. The reaction temperature of the oxidation reaction may vary but is generally from about 20° C. to about 100° C. The preferred reaction temperature ranges from about 25° C. to about 70° C.

Typically the oxidation reaction may be conducted by dissolving the hydroxydiphenylamine in a solvent such as acetone followed by the addition of acetic acid. Aqueous potassium or sodium dichromate is then added between 20° and 50° C. The molar ratio of hydroxydiphenylamine to $Cr_2O_7$ is from about 7:1 to 1:3. Preferably a molar ratio of 2:1 to 1:1 is used. A sufficient amount of acid should be present to solubilize the dichromate. Operable amounts of acid based on the moles of hydroxydiphenylamine range from about 2:1 to 1:3 of hydroxydiphenylamine to moles of acid (based on H+). The N-phenylquinoneimine product forms instantaneously and can be isolated by adding the oxidation solution to excess cold water. The precipitated product is then filtered, washed with water and dried.

The N-phenylquinoneimine is reacted with a primary amine. Examples of suitable amines which may be used in the present invention include methylamine, ethylamine, propylamine, isopropylamine, n-butylamine, sec-butylamine, n-pentylamine, 1-methylbutylamine, 1,2-dimethylpropylamine, 2-methylbutylamine, 3-methylbutylamine, 1-ethylpropylamine, n-hexylamine, 1-methylheptylamine, 1-methylpentylamine, 2-methylpentylamine, 3-methylpentylamine, 4-methylpentylamine, 1,2-dimethylbutylamine, 1,3-dimethylbutylamine, 1-ethylbutylamine, 2-ethylbutylamine, heptylamine, octylamine, nonylamine, decylamine, cyclohexylamine, methylcyclohexylamine, and cyclooctylamine. Of the above amines, isopropylamine, 1,3-dimethylbutyl and cyclohexylamine are preferred.

Additional primary amines which may be used in the present invention are of the formula:

$RNH_2$ 

wherein R is represented by:

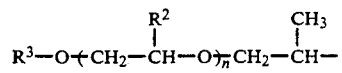

wherein $R^2$ may be the same or different and is independently selected from the group of radicals consisting of hydrogen and an alkyl having 1 carbon atom, $R^3$ is selected from the group of radicals consisting of an alkyl having 1 to 12 carbon atoms and n is an integer of from 0 to 6. Examples of amines of the above formula are commercially available from Texaco Chemical Company under the trademark JEFFAMINE ®. A specific example of such product includes JEFFAMINE ® M-89 having the formula:

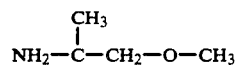

The molar ratio of the N-phenylquinoneimine to the primary amine in the reaction mixture may vary. Generally speaking, the molar ratio of N-phenylquinoneimine to the primary amine ranges from about 1:1 to about 1:10, with a ratio of from about 1:1 to about 1:3 being preferred.

The reaction of the N-phenylquinoneimine with the primary amine may be conducted in the presence or in the absence of a solvent. Examples of solvents which may be used in the present invention include methanol, tetrahydrofuran, ethanol, isopropyl alcohol, benzene, toluene, xylene, methylene chloride, ethylbenzene, cumene, and the like. Preferably, the solvent is methanol, ethanol or isopropyl alcohol. The reaction between the N-phenylquinoneimine and the primary amine may be conducted at a variety of temperatures. Generally speaking, the temperature of the reaction ranges from about 15° C. to about 130° C. with a range of about 20° C. to about 110° C. being preferred depending on the boiling point of the reactants and solvent. In a particularly preferred embodiment, the reaction is conducted at room temperature with methanol.

Examples of N-substituted phenylenediamines which may be prepared according to the present invention include N-phenyl-N'-methyl-p-phenylenediamine, N-phenyl-N'-ethyl-p-phenylenediamine, N-phenyl-N'-propyl-p-phenylenediamine, N-phenyl-N'-isopropyl-p-phenylenediamine, N-phenyl-N'-n-butyl-p-phenylenediamine, N-phenyl-N'-sec-butyl-p-phenylenediamine, N-phenyl-N'-n-pentyl-p-phenylenediamine, N-phenyl-N'-1-methylbutyl-p-phenylenediamine, N-phenyl-N'-(1-methylheptyl)-p-phenylenediamine, N-phenyl-N'-1,2-dimethylpropyl-p-phenylenediamine, N-phenyl-N'-2-methylbutyl-p-phenylenediamine, N-phenyl-N'-3-methylbutyl-p-phenylenediamine, N-phenyl-N'-1-ethylpropyl-p-phenylenediamine, N-phenyl-N'-n-hexyl-p-phenylenediamine, N-phenyl-N'-1-methylpentyl-p-phenylenediamine, N-phenyl-N'-2-methylpentyl-p-phenylenediamine, N-phenyl-N'-3-methylpentyl-p-phenylenediamine, N-phenyl-N'-4-methylpentyl-p-phenylenediamine, N-phenyl-N'-1,2-dimethylbutyl-p-phenylenediamine, N-phenyl-N'-1,3-dimethylbutyl-p-phenylenediamine, N-phenyl-N'-1-ethylbutyl-p-phenylenediamine, N-phenyl-N'-2-ethylbutyl-p-phenylenediamine, N-phenyl-N'-heptyl-p-phenylenediamine, N-phenyl-N'-octyl-p-phenylenediamine, N-phenyl-N'-nonyl-p-phenylenediamine, N-phenyl-N'-decyl-p-phenylenediamine, N-phenyl-N'-cyclooctyl-p-phenylenediamine, N-phenyl-N'-cyclohexyl-p-phenylenediamine, N-phenyl-N'-methylcyclohexyl-p-phenylenediamine, and N-phenyl-N'-cyclooctyl-p-phenylenediamine. Preferably, the N-substituted phenylenediamine is N-phenyl-N'-(1,3-dimethylbutyl)-p-phenylenediamine, N-phenyl-N'-isopropyl-p-phenylenediamine, N-phenyl-N'-(1-methylheptyl)-p-phenylenediamine, and N-phenyl-N'-cyclohexyl-p-phenylenediamine.

The reaction between the N-phenylquinoneimine and the primary amine may be in the presence of or absence of an acidic catalyst. Examples of acid catalysts include methanesulfonic acid, toluenesulfonic acid and the like.

Following the reaction between the N-phenylquinoneimine and the primary amine, various amounts of N-phenyl-N'-diimines may be present. In an effort to further increase the amount of yield of the desired product, the reaction mixture may be hydrogenated. The reaction mixture is hydrogenated to convert the diimines to the desired N-substituted phenylenediamines.

Representative catalysts for the hydrogenation reaction are platinum on carbon, palladium on carbon, Girdler G-22 copper chromite-barium promoted, aqueous sodium hydrosulfite and the like. High temperatures and pressures may be required if the Girdler G-22 catalyst is used. The hydrogenation is preferably done near room temperature with palladium on carbon.

The following examples are included for purposes of illustrating but not limiting the present invention.

EXAMPLE 1

Preparation of N-phenylquinoneimine

Into a suitable reaction vessel, 200 grams of hydroxydiphenylamine was dissolved in 800 ml of acetone at 40° C. 160 grams of acetic acid was added. Into a separate reaction vessel, 320 grams of potassium dichromate (K$_2$Cr$_2$O$_7$) was dissolved in 1800 grams of water. The chromate solution was then added to the reaction vessel containing the hydroxydiphenylamine at a temperature ranging from about 38 to 42° C. Within 25 minutes, 100 percent of the hydroxydiphenylamine was oxidized to N-phenylquinoneimine. The reaction product was stirred below 40° C. for an additional 20 minutes and then 300 ml portions of the reaction mixture were added to 1500 ml portions of ice water and filtered. 175 grams of crude product having a purity of 89.9 percent N-phenylquinoneimine was recovered. Upon subsequent crystallization, following a filtration which removed the salts, the purity was approximately 97.2 weight percent.

EXAMPLE 2

Preparation of N-phenyl-N'-(1,3-dimethylbutyl)-phenylenediamine

Into a one quart reaction vessel was placed 83 grams of 4-phenylquinoneimine (QI) and 375 grams of methanol. To the slurry was added 136 grams of 1,3-dimethylbutylamine. The reaction vessel was maintained at room temperature while rotating on a bottle roller for 4 hours. The reaction product was sampled every hour while following the disappearance of the N-phenylquinoneimine (QI) by area percent gas chromatographic analysis as shown in Table I.

After 4 hours of reaction, the reactor contents were transferred to a one liter autoclave. Then 2 grams of 3% (by weight) palladium on carbon was added and the autoclave pressured with 525 psi of hydrogen. The hydrogenation was conducted between 24° and 30° C. over a 1.5 hour period. The hydrogenated product was filtered and then stripped at a pot temperature of 95° C. and pressure of 5 mm Hg. 125 grams of product was recovered. By gas chromatographic area percent analysis, the product contained 92.7% N-phenyl-N'-(1,3-dimethylbutyl)-p-phenylenediamine. The product was 75.2% by weight of N-phenyl-N'-(1,3-dimethylbutyl)-p-phenylenediamine.

TABLE I

| Component | 1 hour | 2 hours | 3 hours | 4 hours |
|---|---|---|---|---|
| QI | 9.9 | 2.6 | 1.2 | .46 |
| HDPA[1] | — | — | — | — |
| N-phenyl-N'-(1,3-dimethylbutyl)-p-phenylenediimine | 60.0 | 61 | 63.6 | 61 |
| N-phenyl-N'-(1,3-dimethylbutyl)-p-phenylenediamine | 21.0 | 22.0 | 23.4 | 25.5 |
| Unknown | 7.5 | 7.1 | 6.7 | 6.1 |
| Unknown | 1.9 | — | — | — |
| Unknown | — | 1.8 | 2.0 | 3.6 |

[1]Hydroxydiphenylamine

EXAMPLE 3

Preparation of N-phenyl-N'-(1,3-dimethylbutyl)-p-phenylenediamine

Into a 500 ml flask, which was equipped with a thermometer, stirrer, condenser and Dean Stark trap was added 18 grams of N-phenylquinoneimine, 27 grams of 1,3-dimethylbutylamine, 50 grams xylene and 0.5 grams of toluenesulfonic acid. The mixture was heated to 15° C. which was just below the reflux temperature. The reaction was carried out between 115° C. and 123° C. After 45 minutes of reaction, gas chromatographic analysis showed that all of the N-phenylquinoneimine had reacted with the 1,3-dimethylbutylamine. The reaction was stopped after 1½ hours of reaction. The product was then washed with about 35 grams of Na$_2$S$_2$O$_4$ in aqueous solution to reduce any N-phenyl-N'-(1,3-dimethylbutyl)-p-phenylenediimine to N-phenyl-N'-(1,3-dimethylbutyl)p-phenylenediamine. The aqueous portion was removed and the product filtered. The volatiles were removed by stripping the product to a pot temperature of 100° C. at 4 mm Hg. 20 grams of N-phenyl-N'-(1,3-dimethylbutyl)-p-phenylenediamine were removed.

EXAMPLE 4

Preparation of N-phenyl-N'-(1,3-dimethylbutyl)-p-phenylenediamine

Into a 8 ounce bottle was weighed 20 grams of N-phenylquinoneimine, 150 ml methanol and 33 grams of 1,3-dimethylbutylamine. The bottle was capped and allowed to rotate at room temperature on a bottle roller for 4.5 hours. Area percent gas chromatographic analysis showed that the reaction contained 68% of N-phenyl-N'-(1,3-dimethybutyl)-p-phenylenediimine, 27% of N-phenyl-N'-(1,3-dimethylbutyl)-p-phenylenediamine and 5.0% of unknowns. The reaction bottle contents were transferred to a 300 ml hydrogenation apparatus followed by the addition of 2.5 grams of 3% palladium on carbon and 20 ml of methanol. The apparatus was pressured with 49 psi of hydrogen and agitated for two hours while consuming 75 psi of hydrogen. The hydrogenation temperature rose rapidly to 41° C. and then dropped to 27° C. The reactor contents were filtered and then stripped to a pot temperature of 95° C. to remove the volatiles. 29 grams of N-phenyl-N'-(1,3-dimethylbutyl)-p-phenylenediamine were recovered.

EXAMPLE 5

Preparation of N-phenyl-N'-cyclohexyl-p-phenylenediamine

Into a three neck 500 ml flask equipped with a thermometer, stirrer, Dean Stark trap and condenser was charged 18.4 grams of N-phenylquinoneimine, 150 ml toluene, 19.9 cyclohexylamine and 5 drops methanesulfonic acid. The reaction was conducted at 110° C. for 1.5 hours after which time the product was washed with 200 ml water containing 10 grams of Na$_2$S$_2$O$_4$. The product was decanted, filtered and stripped at a pot temperature of 100° C. at 4 mm Hg. 27 grams of N-phenyl-N'-cyclohexyl-p-phenylenediamine were recovered.

EXAMPLE 6

Preparation of N-phenyl-N'-(1-methyl-2-methoxyethyl)-p-phenylenediamine

Into a four-ounce bottle was weighed 2 grams of N-phenylquinoneimine, 25 grams of methanol and 3 grams of methoxypropylamine (JEFFAMINE® M-89). The bottle was capped, allowed to rotate at room temperature on a bottle roller for 19 hours. The reaction was followed by gas chromatography which indicated disappearance of the N-phenylquinoneimine and formation of the desired product.

What is claimed is:

1. An N-substituted phenylenediamine of the formula:

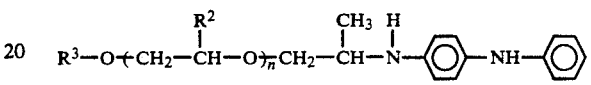

wherein $R^2$ may be the same or different and is selected from the group of radicals consisting of hydrogen and an alkyl having 1 carbon atom, $R^3$ is selected from the group of radicals consisting of an alkyl having 1 to 12 carbon atoms and n is an integer of from 0 to 6.

2. The compound of claim 1 wherein n is 0 and $R^3$ is an alkyl having 1 carbon atom.

* * * * *